(12) United States Patent
Roewer et al.

(10) Patent No.: US 9,006,215 B2
(45) Date of Patent: Apr. 14, 2015

(54) PHARMACEUTICAL PREPARATION COMPRISING PROPOFOL SALT AND CYCLODEXTRIN

(76) Inventors: Norbert Roewer, Wurzburg (DE); Jens Broscheit, Wurzburg (DE)

( * ) Notice: Subject to any disclaimer, the term of this patent is extended or adjusted under 35 U.S.C. 154(b) by 0 days.

(21) Appl. No.: 13/983,107

(22) PCT Filed: Mar. 1, 2012

(86) PCT No.: PCT/IB2012/000391
§ 371 (c)(1),
(2), (4) Date: Aug. 1, 2013

(87) PCT Pub. No.: WO2012/104730
PCT Pub. Date: Aug. 9, 2012

(65) Prior Publication Data
US 2013/0316976 A1 Nov. 28, 2013

(30) Foreign Application Priority Data
Feb. 4, 2011 (EP) .................................... 11153452

(51) Int. Cl.
*A61K 47/48* (2006.01)
*A61K 31/05* (2006.01)
*A61K 47/40* (2006.01)
*A61K 9/00* (2006.01)

(52) U.S. Cl.
CPC ....... *A61K 47/4823* (2013.01); *A61K 47/48969* (2013.01); *A61K 9/0019* (2013.01); *A61K 31/05* (2013.01)

(58) Field of Classification Search
None
See application file for complete search history.

(56) References Cited

U.S. PATENT DOCUMENTS 7,034,013 B2 * 4/2006 Thompson et al. ............. 514/58

FOREIGN PATENT DOCUMENTS

| EP | 2106786 A1 | 10/2009 |
| WO | 96/32135 A1 | 10/1996 |
| WO | 02/074200 A1 | 9/2002 |
| WO | 03/080079 A1 | 10/2003 |

OTHER PUBLICATIONS

Vierstein, H. et al "Preparation and central action of propofol . . . " Arzneim.-Forsch./Drug Res. (1993) vol. 43(II) No. 8, pp. 818-821.*
Jara et al. "The interaction of solvatochromic pyridiniophenolates with cyclodextrins." Tetrahedron. 62. (2006): 7817-7823.
Eftink et al. "Calorimetric studies of p-nitrophenol binding to alpha- and beta-cyclodextrin", Bioorganic Chemistry, Academic Press Inc., 10. (1981): 388-398.

* cited by examiner

Primary Examiner — Leigh Maier
(74) Attorney, Agent, or Firm — Casimir Jones, S.C.

(57) ABSTRACT

The invention relates to a pharmaceutical formulation that contains a complex of a propofol salt with a cyclodextrin. The invention makes it possible to provide propofol in a formulation that can be stored and that can be administered intravenously without problems.

21 Claims, No Drawings

PHARMACEUTICAL PREPARATION COMPRISING PROPOFOL SALT AND CYCLODEXTRIN

This application is a §371 US National Entry of International Application No. PCT/IB2012/000391, filed Mar. 1, 2012, which claims the benefit of European Application No. 11 153 452.5, filed Feb. 4, 2011, each of which is incorporated herein by reference in its entirety.

The invention relates to a pharmaceutical formulation which comprises propofol.

In pharmacy, it is a frequent problem to formulate a pharmaceutical active ingredient such that it is administered at the intended site of action in the desired concentration and as efficiently as possible by means of a specific type of application. Thus, an active ingredient intended for intravenous application must be soluble in water to a certain extent so that a systemic concentration in the blood can be achieved at all. On the other hand, it must generally have a certain lipophilicity in order, if appropriate, to be able to penetrate cell membranes at the intended site of action. A merely readily water-soluble active ingredient can, for example, build up a high systemic concentration in the blood following intravenous application, but, for example in the event of excessively low lipophilicity, it will have low bioavailability since passage through the cell membrane is possibly inadequate at the intended site of action.

Propofol is an intravenous anesthetic tested in clinical practice for the first time in 1977. Propofol is a scarcely water-soluble anesthetic active ingredient which has to be rendered accessible to intravenous administration.

The solution of the anesthetic in a fatty emulsion (trade name Diprivan®) was able to reduce the vein pain often observed with i.v. administration, and so propofol was introduced into clinical practice in 1989.

This propofol lipid emulsion comprises soybean oil, glycerol and egg phosphatides. Vein pain upon injection is a problem that continues to arise often. Moreover, it can lead to serious allergic reactions. Since the formulation as a fatty emulsion favors microbial growth, contamination of the emulsion can lead, even after short storage times, to sepsis after administration.

The object of the invention is to provide a pharmaceutical formulation of the type mentioned at the start which permits trouble-free intravenous administration and has the specified disadvantages to a lesser extent, if at all.

This object is achieved by complexing propofol as salt with a cyclodextrin. Propofol can be converted to a salt in an alkaline medium. The propofol anion can be complexed by a cyclodextrin. Within the context of the invention, the term propofol salt refers to the anion of propofol (phenolate), which can be complexed by the cyclodextrin. In the complex according to the invention, propofol is thus present in complexed form as an anion.

Surprisingly, it has been found that a stable, injectable, pharmaceutical formulation with a high propofol concentration can be prepared in this way. The pharmaceutical formulation according to the invention can be provided as an aqueous solution suitable for injection. Alternatively, it is possible, after preparing the complex, to draw off the solvent and to provide the complex as a storable solid. Prior to administration, this solid is converted again to an aqueous solution.

The pH of an aqueous solution of the complex is preferably above 7, further preferably above 8, further preferably above 9. Preferred upper limits for the pH are 11 or 10. Particular preference is given to a pH range of 8-11, further preferably 9-11, further preferably 9-10. If the complex is provided as a storable solid, a pH from the stated ranges is preferably established following resolubilization in water.

According to the invention, the cyclodextrin used for complexing the propofol is particularly preferably 2-hydroxypropyl-beta-cyclodextrin (HPBCD). The propofol salt used is preferably an alkali metal salt, particularly preferably a sodium salt.

The molar ratio of propofol salt and cyclodextrin to one another is preferably 1:2 to 1:6, further preferably 1:2 to 1:4, further preferably about 1:2. The propofol salt content of the complex is preferably about 4 to 9% by weight.

The invention also provides a process for preparing a pharmaceutical formulation according to the invention. According to the invention, firstly an alkaline aqueous solution of the cyclodextrin is prepared. Propofol is added to this alkaline solution and mixed, preferably with stirring, to the point of dissolution and complexation. This preferably takes place under an inert gas atmosphere. According to the invention, it is likewise possible to establish alkaline conditions only after the propofol has been added to the cyclodextrin.

The dissolution and complexation of propofol takes place preferably over a period of 2 to 10 h, further preferably 3 to 5 h, further preferably about 4 h. According to the invention, the dissolution and complexation process takes place essentially more quickly than in the case of the complexation of the phenolic form of propofol. A significantly higher concentration of the propofol in the complex can also be established.

In a further step, the solution obtained according to the invention can be freed from remaining solids fractions, for example filtered. Of suitability is e.g. a filtration through a pore filter with the pore size 0.45 μm.

The solvent can be drawn off from the solution prepared according to the invention by known and suitable processes such as, for example, freeze-drying. The complex is provided in this way as a storable and resolubilizable solid.

One working example of the invention is explained below.

The specifications of all of the materials used correspond to the European Pharmacopeia (Ph. Eur.). The following feed substances were used:
propofol
NaOH
HPBCD
water for injection purposes NaOH was prepared with 60 ml of water to give a 0.01 N NaOH solution. 12 g of HPBCD were added thereto and dissolved with stirring. Then, 0.817 g of propofol were added and the mixture was stirred for a further 4 h at 40-80 min$^{-1}$ until the evolving propofol salt was dissolved and complexed. The resulting solution has a pH of 9-10.

The solution obtained was filtered through a pore filter with a pore size of 0.45 μm. After the filtration, the solution was lyophilized. This gave a white powder. The complex obtained can be characterized as follows:
Water content: 1.4% by weight
pH of a 1% strength aqueous 9.5 solution:
Propofol content (calculated as 6.5% by weight active phenol form):
Solubility of the complex in water: 41% by weight
Resolubilization of the complex in water gives an aqueous solution with a content of active propofol of 46 mg/ml.

The invention claimed is:

1. A pharmaceutical formulation which comprises a complex of a propofol salt with a cyclodextrin, wherein the propofol salt content of the complex is 4 to 9% by weight.

2. The formulation as claimed in claim 1, characterized in that the cyclodextrin is 2-hydroxypropyl-β-cyclodextrin (HPBCD).

3. The formulation as claimed in claim 1, characterized in that the propofol salt is an alkali metal salt.

4. The formulation as claimed in claim 3, characterized in that the propofol salt is a sodium salt.

5. The formulation as claimed in-claim 1, characterized in that the propofol salt: cyclodextrin molar ratio is 1:2 to 1:6.

6. The formulation as claimed in claim 1, wherein the propofol salt: cyclodextrin molar ratio is 1:2 to 1:4.

7. The formulation as claimed in claim 1, wherein the propofol salt: cyclodextrin molar ratio is about 1:2.

8. The formulation as claimed in claim 1, characterized in that said formulation is an aqueous solution suitable for injection.

9. The formulation as claimed in claim 8, characterized in that the pH is between 8 and 11.

10. The formulation as claimed in claim 8, characterized in that the pH is between 9 and 11.

11. The formulation as claimed in claim 8, characterized in that the pH is between 9 and 10.

12. The formulation as claimed in claim 1, characterized in that the formulation is a water-soluble solid.

13. A process for preparing a formulation as claimed in claim 1, characterized by the steps:

a) preparing an alkaline aqueous solution of the cyclodextrin, b) dissolving propofol in the alkaline aqueous solution to produce an aqueous solution of said complex, characterized in that said aqueous solution of said complex has a pH above 8.

14. The process as claimed in claim 13, characterized in that the dissolution of the propofol takes place under an inert gas atmosphere.

15. The process as claimed in claim 13, characterized in that the dissolution of the propofol takes place over a period of from 2 to 10 h.

16. The process as claimed in claim 13, characterized in that the dissolution of the propofol takes place over a period of from 3 to 5 h.

17. The process as claimed in claim 13, characterized in that the dissolution of the propofol takes place over a period of about 4 h.

18. The process as claimed in claim 13, characterized in that the solution obtained in step b) is filtered.

19. The process as claimed in claim 13, characterized in that water is removed from the solution obtained in step b).

20. The process as claimed in claim 19, characterized in that said water is removed by freeze-drying.

21. A process for providing an anesthetic to an intended site of action, comprising: providing a formulation as claimed in claim 1 and administering said formulation at the intended site of action.

* * * * *